United States Patent [19]

Felix

[11] Patent Number: 5,350,856
[45] Date of Patent: Sep. 27, 1994

[54] 2-(SUBSTITUTED IMINO)-1,3,4-DIHYDROTHIADIAZOLES

[75] Inventor: Raymond A. Felix, Richmond, Calif.

[73] Assignee: ICI Americas Inc., Wilmington, Del.

[21] Appl. No.: 463,190

[22] Filed: Jan. 10, 1990

Related U.S. Application Data

[60] Division of Ser. No. 215,281, Jul. 8, 1988, Pat. No. 4,911,745, which is a continuation-in-part of Ser. No. 77,477, Jul. 24, 1987, abandoned.

[51] Int. Cl.$^5$ .......................................... C07D 285/135
[52] U.S. Cl. .................................. 548/138; 548/139; 548/140
[58] Field of Search ........................ 548/138, 139, 140

[56] References Cited

U.S. PATENT DOCUMENTS

| 2,783,239 | 2/1957 | Young et al. | 548/135 |
| 3,207,754 | 9/1965 | Clarkson | 548/141 |
| 4,518,414 | 5/1985 | Schirmer et al. | 548/135 |
| 4,719,001 | 1/1988 | Dvoracek | 548/135 |

OTHER PUBLICATIONS

Shawali, A. S., H. M. Hassaneen and N. F. Eweiss, *J. Appl. Chem. Biotechnol.*, 28, 864–868 (1978).
Shawali, A. S. and C. Parkanyi, *J. Heterocyclic Chem.* 17: 833–854 (1980).
Tewari, R. S., P. Arihar and P. D. Dixit, *J. Chem. Eng. Data*, 1983, 28:281–282.
Tewari, R. S., P. D. Dixit and Ajay K. Dubey, 1983, 28:283–285.
Hassaneen, H. M., A. M. Farag and A. S. Shawali, *J. Heterocyclic Chem.*, 24:577 (1987).
Potts, *Comprehensive Heterocyclic Chemistry*, p. 570 (1984).
Metzger, Thiazoles and its Deriavtives V. 1 p. 298 (1979).
Potts, Comprehensive Heterocyclic Chemistry No. 6 p. 577 (1984).

*Primary Examiner*—Robert Gerstl
*Attorney, Agent, or Firm*—William E. Dickheiser

[57] ABSTRACT

This invention relates to a process for producing a compound of the formula

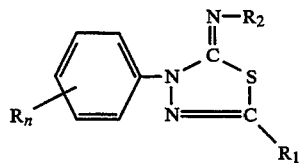

comprising reacting a compound having the formula

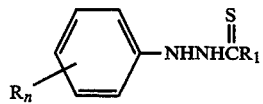

with cyanogen chloride or cyanogen bromide.

3 Claims, No Drawings

2-(SUBSTITUTED IMINO)-1,3,4-DIHYDROTHIADIAZOLES

CROSS REFERENCE TO RELATED APPLICATIONS

This is a divisional of application Ser. No. 07/215,281, filed Jul. 8, 1988, now U.S. Pat. No. 4,911,745, which is a continuation-in-part of application Ser. No. 077,477, filed Jul. 24, 1987, now abandoned.

This invention relates to novel herbicidal compounds of the dihydrothiadiazole type, having the formula

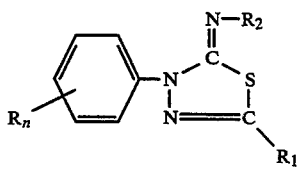

in which

R is halo, trihalomethyl, penthaloethyl, mono- or difluoromethyl, mono-, di-, tri- or tetrafluoroethyl, fluoroalkylthio, fluoroalkoxy, methylthio, methylsulfonyl, halomethylsulfonyl, $C_1$-$C_2$ alkyl, or methoxy;

n is 0, 1 or 2, provided that:
(a) if n is 1 and R is other than fluoro, the substituent R is located at the 3-position on the phenyl ring; and
(b) if n is 2, the substituents R are located at the 3- and 4-positions on the phenyl ring;

$R_1$ is hydrogen, $C_1$-$C_3$ alkyl, $C_1$-$C_3$ alkoxy, $C_1$-$C_2$ alkylthio, $C_3$-$C_4$ alkenylthio, $C_1$-$C_4$ alkylsulfonyl, $C_1$-$C_4$ alkylsulfinyl, cyano, carbamyl, $C_1$-$C_4$ mono-alkylcarbamyl, $C_1$-$C_2$ carboalkoxy, or $NR_3R_4$ in which $R_3$ and $R_4$ are independently hydrogen, $C_1$-$C_4$ alkyl or $C_2$-$C_4$ alkenyl; and $R_2$ is phenyl; mono- or disubstituted phenyl in which the substituents are selected from halo, cyano, and trihalomethyl; $C_1$-$C_4$ mono- or dialkylcarbamyl; phenylcarbamyl; $C_1$-$C_4$ mono-alkylthiocarbamyl; $C_4$-$C_6$ keto alkenyl; cyano; $C_1$-$C_4$ alkylsulfonyl; $C_1$-$C_4$ haloalkylsulfonyl; or

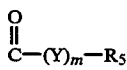

in which Y is oxygen or sulfur; m is 0 or 1; and $R_5$ is $C_1$-$C_{10}$ alkyl; $C_2$-$C_{10}$ alkenyl; $C_2$-$C_8$ alkynyl if m is 0; $C_3$-$C_8$ alkynyl in which the triple bond is separated from the oxygen or sulfur atom (Y) by at least one methylene group if m is 1; $C_1$-$C_8$ haloalkyl if m is 0; $C_2$-$C_8$ haloalkyl if m is 1; $C_2$-$C_{10}$ alkoxyalkyl if m is 0; pryidyl if m is 0; $C_3$-$C_{10}$ alkoxyalkyl in which the alkylene portion has at least two carbon atoms if m is 1; or $R_5$ is

in which p is 0 or 1, $R_6$ is a $C_1$-$C_2$ alkylene group and $R_7$ is phenyl, halosubstituted phenyl; $C_3$-$C_7$ cycloalkyl, optionally substituted by from 1 to 3 methyl group; $C_1$-$C_6$ carboalkoxy; or a saturated or unsaturated heterocyclic ring containing from 5 to 6 atoms including from 1 to 2 hetero atoms selected from oxygen and sulfur, optionally substituted by from 1 to 3 methyl groups and optionally substituted by from 1 to 2 oxo groups; provided that when $R_1$ is methylthio and $R_2$ is isopropylcarboxy, then R is not 2-fluoro.

In the above definition, the term "halo" includes fluoro, chloro, bromo and iodo.

When the phenyl ring shown in the basic structure is disubstituted (n=2) the two substituents may be the same or different, and are chosen from among those mentioned in the definition of the moiety R. When the phenyl ring is mono-substituted, the substituent R is preferably at the meta-position.

The term "alkyl" refers to straight and branched chain acyclic hydrocarbyl moieties having the number of carbon atoms associated with that term whenever used (i.e., by itself or as part of the definition of another moiety, e.g., "haloalkyl", "alkylthio," etc.). Examples of alkyl groups include methyl, ethyl, n-propyl, isopropyl, n-butyl, isobutyl, sec-butyl, tert-butyl, and the various pentyl, hexyl, etc. moieties. The term "iso-$C_5$-$H_{11}$" (isoamyl or isopentyl) designates the group 3-methylbutyl. The term "sec-$C_5$-$H_{11}$" designates the 2-pentyl group.

The term "carboalkoxy" refers to moieties of the specified number of carbon atoms, having the structure

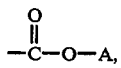

in which A represents an alkyl group, alkylalkoxy and alkylcarboalkoxy having the required number of carbon atoms. Such examples of carboalkoxy moieties include carbomethoxy, carboethoxy, 1-methyl-carbomethoxymethyl and the like.

The terms "akylcarbamoyl" and "alkylthiocarbamyl" refer respectively to moieties having the structures

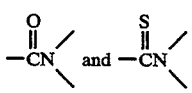

in which the nitrogen atom is further substituted by one or two alkyl groups, as defined, the alkyl groups containing the indicated number of carbon atoms. In dialkylcarbamyl compounds of this invention the two alkyl groups may be the same or different. The term "carbamyl" when used by itself refers to the unsubstituted moiety

Examples of such substituted groups include methylcarbamyl, ethylcarbamyl, dimethylcarbamyl, N-methyl-N-ethylcarbamyl, and the like.

The term "alkenyl" refers to straight and branched chain mono- or polyunsaturated acyclic hydrocarbyl moieties with the number of carbon atoms as specified. Examples of alkenyl groups include vinyl, allyl, propenyl, isopropenyl, isobutenyl, and the like. The term "ketoalkenyl" refers to an alkenyl group in which one carbon atom is doubly bonded to an oxygen atom. One example is 3-keto-1-butenyl. The term "alkynyl" refers to straight and branched chain acyclic hydrocarbyl moieties having at least one triple bond. One example is propargyl (2-propynyl).

The term "cycloalkyl" refers to saturated cyclic hydrocarbyl moieties having the specified number of carbon atoms and includes cyclopropyl, cyclobutyl, cyclopentyl, cyclohexyl, and cycloheptyl.

The term "haloalkyl" refers to alkyl groups or alkoxy groups having the indicated number of carbon atoms, substituted by one or more halogen atoms, which may be the same or different. When unspecified, the terms "haloalkyl" and "alkoxy" are meant to refer to alkyl groups or alkoxy groups ranging from monohalo-alkyl or monofluoroalkoxy to fully substituted halo-alkyl groups. Examples of haloalkyl and fluoroalkoxy groups include chloromethyl, dichloromethyl, difluoromethoxy, trifluoromethyl, trifluoromethoxy, 2-chloroethyl, pentafluoroethyl, pentafluoroethoxy, heptafluoropropyl, heptafluoropropoxy, 3-chloropropyl, 2,2,2-trifluoro-1-methylethyl, 2,2,2-trifluoro-1-methylethoxy, 1,1,2,2-tetrafluoroethoxy and the like. The term "haloalkylsulfonyl" indicates a sulfonyl group bonded to a haloalkyl group, for instance, chloromethylsulfonyl.

The term "alkoxyalkyl" indicates an alkyl group substituted by an alkoxy group, for instance, methoxymethyl, methoxyethyl, ethoxyethyl, and the like. The indicated number of carbon atoms refers to the total number of carbon atoms in the alkoxyalkyl group (e.g., $C_2$ for methoxymethyl, $C_3$ for ethoxymethyl and the like). When $R_5$ is alkoxyalkyl and m is 0, the oxygen atom in the alkoxyalkyl group may be positioned anywhere in the chain. When m is 1, however, there must be at least two carbon atoms in the "alkylene" portion of the alkoxyalkyl group; that is, there must be at least two carbon atoms separating the oxygen or sulfur atom represented by the symbol "Y" and the oxygen atom of the alkoxyalkyl group (i.e., the alkoxyalkyl group is at least an alkoxyethyl group).

The value of p may be 0 or 1. When p is 0 there is a direct linkage between the group $R_7$ and the group

When p is 1, $R_7$ and the group

are linked by a $C_1$–$C_2$ alkylene, e.g., methylene or 1,1- or 1,2-ethylene, group.

The heterocyclic rings included in the definition of $R_7$ may be saturated or may be mono-, di- or tri-unsaturated. Such rings will contain one or two oxygen or sulfur atoms, for instance, furanyl, tetrahydrofuranyl, tetrahydropyranyl, 1,3-dioxolanyl, 1,3-dioxanyl, 1,4-dioxanyl, tetrahydrothienyl, pyridyl and the like, optionally substituted with from 1 to 3 methyl groups. In addition or alternatively to the methyl substitution, the heterocyclic ring may have one or more oxygen atoms doubly bonded to carbon or sulfur atoms in the ring.

Preferred substituents are: for $R_n$—meta-halo, -trihalomethyl, fluoroalkoxy or fluoroalkylthio, particularly meta-chloro, -fluoro, -trifluoromethyl, difluoromethoxy, tetrafluoroethoxy, and -trifluoromethylthio, 3-chloro, 4-fluoro and 3-trifluoromethyl, 4-fluoro; for $R_1$—alkyl (especially methyl or ethyl), alkoxy (especially methoxy), methylthio and dimethylamino; and for $R_2$—4-fluorophenyl, monoalkylcarbamyl (especially methyl-, ethyl-, n-propyl- and isopropylcarbamyl), alkylcarbonyl ($R_5$ is alkyl, m is 0, including both straight and branched chain alkyl groups, especially $C_1$–$C_6$ alkyl such as methyl-, ethyl-, n-propyl-, isopropyl-, isobutyl- and 2-methylbutylcarbonyl), carboalkoxy ($R_5$ is alkyl, m is 1, Y is oxygen, including both straight and branched chain alkyl groups, especially $C_1$–$C_6$ alkyl such as carbomethoxy, carboethoxy, carbo-n-propoxy, carboisopropoxy, carboisobutoxy and the like), $C_2$–$C_8$ haloalkylcarbonyl ($R_5$ is haloalkyl, particularly polyfluoro-$C_2$–$C_5$ alkyl, and m is 0), $C_1$–$C_8$ carbo-(haloalkoxy) ($R_5$ is haloalkyl, particularly chloro- and fluoro-$C_2$–$C_5$ alkyl, m is 1 and Y is oxygen), optionally methyl-substituted cycloalkylcarbonyl ($R_5$ is $(R_6)_pR_7$, p is 0, m is 0, $R_7$ is cycloalkyl, particularly cyclopropyl, cyclopentyl, methylcyclopentyl or cyclohexyl), optionally methyl-substituted carbocycloalkoxy ($R_5$ is $(R_6)_pR_7$, p is 0, m is 1, Y is oxygen, $R_7$ is cycloalkyl, particularly cyclopropyl, cyclopentyl, methylcyclopentyl or cyclohexyl), optionally methylsubstituted cycloalkylmethylcarbonyl ($R_5$ is $(R_6)_pR_7$, p is 1, m is 0, $R_6$ is methylene, $R_7$ is as above for cycloalkyl), optionally methyl-substituted carbo-cycloalkylmethoxy ($R_5$ is $(R_6)_pR_7$, p is 1, m is 1, Y is oxygen, $R_6$ is methylene, $R_7$ is as above for cycloalkyl), heterocyclic carbonyl ($R_5$ is $(R_6)_pR_7$, p is 0, m is 0, and $R_7$ is a 5- or 6-member heterocyclic ring containing 1 or 2 oxygen and/or sulfur atoms, optionally substituted by from 1 to 3 methyl groups and optionally substituted by 1 or 2 oxo groups, particularly furanyl, tetrahydrofuranyl, tetrahydropyranyl, dioxolanyl, dioxanyl, tetrahydrothienyl, tetrahydro-1-oxothienyl, 2,2-dimethyl-1,3-dioxolanyl and the like), carbo-heterocyclic-oxy ($R_5$ is $(R_6)_pR_7$, p is 0, m is 1, Y is oxygen, and $R_7$ is a heterocyclic ring as described above), heterocyclic-methyl-carbonyl (p is 1, m is 0, $R_6$ is methylene, $R_7$ is heterocyclic) and carbo-(heterocyclic-methoxy) (p is 1, m is 1, Y is oxygen, $R_6$ is methylene and $R_7$ is heterocyclic).

When it is indicated that a phenyl ring may be di- or further substituted, the substituents may be the same or different, and are selected from the specified groups. When no specific position of substitution is mentioned on a phenyl ring, it is intended that the substituent or substituents may be substituted at any position on the ring.

The compounds of this invention have been found to be active herbicides, possessing pre- and/or post-emergence herbicidal activity against various types of weeds, including broadleaf and grassy weeds. As mentioned hereinbelow, some of the compounds demonstrate selective control of weeds in certain crops, such as cereals, including wheat, rice, barley, and in cotton.

This invention therefore also relates to a method for controlling undesirable vegetation comprising applying to a locus where control of such vegetation is desired, either prior to subsequent to the emergence of such vegetation, a herbicidally effective amount of a compound as described herein, and also relates to herbicidal compositions comprising a herbicidally effective amount of a compound as described herein, together with an inert diluent or carrier suitable for use with herbicides.

As used herein, the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

There are several processes by which the compounds of this invention may be prepared. Some of these processes, as well as intermediates, are also novel and form other aspects of this invention.

Process A: Reaction of A Substituted Thionohydrazine with an Imidoyl Dihalide

In this process, the appropriate thionohydrazine is reacted with an imidoyl dihalide in the presence of a base according to the reaction:

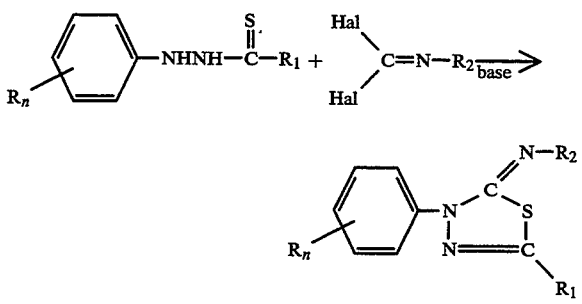

in which R, $R_1$, $R_2$, and n are as previously described and Hal stands for a halogen, preferably chlorine. Both halogens (Hal) are identical. This reaction is conducted at a temperature of from about $-100°$ C. to about $+150°$ C., preferably from about $-78°$ C. to about $-80°$ C. Suitable bases include trialkylamines, preferably tri-lower alkylamines such as triethylamine, pyridine, alkali metal hydrides (preferably sodium hydride) and alkali metal tertiary alkoxides such as sodium and potassium tertiary butoxides. The reaction may be carried out in the presence of a solvent. Suitable solvents include dimethylformamide, tetrahydrofuran, 1,2-dichloroethane, and benzene.

This method is the preferred process for the production of arylimino compounds ($R_2$ is phenyl or substituted phenyl), but may be used for production of all compounds of this invention.

The starting materials for this process are readily available. The imidoyl dihalides may be prepared according to the literature, for instance by reaction of formanilides with thionyl chloride and sulfuryl chloride. The thionohydrazines are prepared as described below.

All intermediates and final products in the examples which follow, as well as those which appear subsequently, were identified by typical spectroscopic methods, including nuclear magnetic resonance, infrared and mass spectroscopy.

The following are examples of production of compounds by process A.

EXAMPLE 1

2-(4-Fluorophenyl)imino-3-(3-trifluoromethyl)phenyl-5-methoxy-2,3-dihydro-1,3,4-thiadiazole (Compound 99 herein)

a) Production of the Thionohydrazine.

In a 100 milliliter (ml) flask were placed 6.5 grams (g) (0.03 mole) of 25% sodium methoxide and 2.3 g (0.03 mole) of carbon disulfide. This mixture was stirred 20 minutes and 10 ml water and 3.5 g (0.03 mole) of chloroacetic acid sodium salt were added and stirred one hour. Most of the solvent was then removed under vacuum and replaced with 10 ml methanol and 4.4 g (0.025 mole) (3-trifluoromethyl)phenyl hydrazine. This mixture was then heated on a steam bath for 0.5 hour and the solvent stripped. The residue was dissolved in ether, washed with water, phase separated, dried and stripped to yield 5 g of solids.

b). In a 100 ml flask were placed 2.5 g (0.01 mole) of the intermediate obtained in step (a), 15 ml of 1,2-dichloroethane, and 1.9 g (0.01 mole) of 4-fluorophenyl imidoyl dichloride. This stirred solution was cooled in an ice bath and 2.8 ml (0.02 mole) of triethylamine added. The mixture was stirred cold 0.5 hour then refluxed 0.5 hour. The solution was washed with water, phase separated, dried and stripped. The residue was treated with 50 ml of hot hexane, decanted and allowed to cool. The solids were collected to yield 2.2 g (m.p. 113°–115° C.) identified as the expected product.

Process B:

Compounds of this invention in which $R_2$ is $C_1$–$C_4$ alkylcarbamyl, phenylcarbamyl, alkylthiocarbamyl, cyano, ketoalkenyl, alkylsulfonyl, haloalkylsulfonyl, or

in which Y, m and $R_5$ are as defined above, may be prepared by a two-step process represented by the scheme:

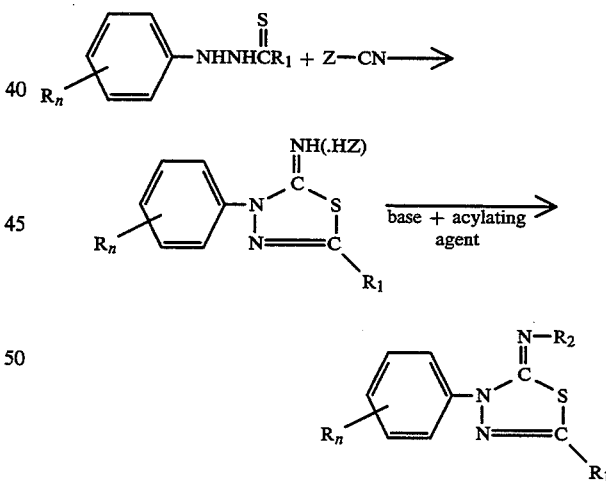

In the first step of this process, a 2-imino-3-(substituted) phenyl thiadiazole is prepared by cyclization of a phenyl thionohydrazine having the formula

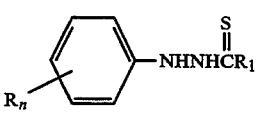

with a cyanogen halide having the formula Z-CN in which Z is chloro or bromo. The cyclization reaction is conducted in the presence of an inert solvent such as diethyl ether, a chlorinated hydrocarbon solvent (e.g., methylene chloride, chloroform or 1,2-dichloroethane) or a hydrocarbon solvent such as toluene. Temperatures may range from about −50° C. to about +150° C., and are preferably from about 0° C. to about 25° C. The process when carried out in this manner produces the hydrohalide product of the intermediate iminothiadiazole, which is indicated by the use of the term "(.HZ)" in the above equation. In an alternative embodiment this cyclization reaction may be run in the presence of a suitable base such as sodium hydride or a tertiary amine to produce the free iminothiadiazole intermediate, or the free intermediate may be produced by neutralization of the hydrohalide salt at the completion of the reaction. The iminothiodiazole intermediates, and their hydrohalide salts are novel, and may also have herbicidal activity. The iminothiadiazoles correspond to the general formula

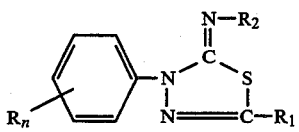

in which R, n and $R_1$ are as previously defined and $R_2$ is hydrogen.

In the second step of this process the intermediate iminothiadiazole compound (as the free compound or the hydrohalide salt) is reacted with the appropriate acylating agent in the presence of a suitable base. If the desired product is one in which $R_2$ has the formula

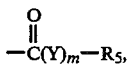

the acylating agent has the formula

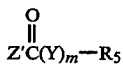

in which Z' is a halogen, preferably chloro, bromo or iodo. If the desired product is one in which $R_2$ is $C_1$-$C_4$ alkylcarbamyl, $C_1$-$C_4$ alkylthiocarbamyl or phenylcarbamyl, the acylating agent is the appropriate isocyanate or isothiocyanate ($R_9NCO$ or $R_9NCS$ in which $R_9$ is $C_1$-$C_4$ alkyl or phenyl). If the iminothiadiazole intermediate is used in the form of its hydrohalide salt, one molar equivalent of the base is required. Suitable bases include amines, sodium hydroxide and sodium bicarbonate. This acylation reaction may be carried out in the presence of a solvent typically used for acylation reactions, for instance, toluene, methylene chloride or diethyl ether. The temperature of the acylation reaction may be from about −50° C. to about +150° C., preferably from about 0° C. to about 25° C.

The substituted phenyl thiono hydrazines

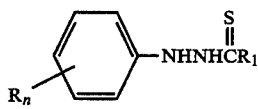

in which n=1 or 2 are also novel. They may be prepared in several ways, depending on the definition of $R_1$.

Thiono hydrazines in which $R_1$ is alkylthio or alkenylthio can be prepared by reaction of a substituted phenyl hydrazine with carbon disulfide in the presence of a base and an alkylating agent such as an alkyl or alkenyl halide (iodide, chloride or bromide), sulfate, etc. This reaction is conducted at a temperature generally from about −50° C. to about +150° C., preferably from about 0° C. to about 25° C. The solvent may be used which is inert to the reactants or product, for example, diethyl ether, tetrahydrofuran, toluene or benzene. The base is preferably a weak base such as a trialkylamine, pyridine, or potassium carbonate.

Thiono hydrazines in which $R_1$ is alkoxy may be prepared by reaction of the appropriate substituted phenyl hydrazine with a dithiocarbonate

in which $R_1$ is $C_1$-$C_3$ alkoxy and $R_8$ is a $C_1$-$C_4$ alkyl or methylcarboxy group. This reaction is again carried out at temperatures of from about −50° C. to about +150° C., preferably from about 80° C. to about 110° C. The reaction may be run with or without solvent. If run with a solvent, inert solvents such as toluene, tetrahydrofuran, alcohol or alcohol-water mixtures may be employed. The dithiocarbonate may be produced by reaction of an alkali metal alkoxide with carbon disulfide in the presence of an alkylating agent which introduces the group $R_8$. This reaction can be carried out in neat alcohol, ethereal solvents such as tetrahydrofuran or dimethyl ether or other inert solvents, for instance dimethylformamide. The temperature may be from about −50° C. to about +150° C., preferably from about 60° C. to about 80° C. The group $R_8$ is preferably one which is readily replaced as $R_8S-$ at a later step in the overall process. Consequently, $R_8$ is preferably a small group or groups such that the overall group $R_8SH$ is a good leaving group and is either volatile or water soluble.

Thiono hydrazine in which $R_1$ is a $C_1$-$C_3$ alkyl group are preferably made by reaction of the appropriate substituted phenyl hydrazide with phosphorus pentasulfide. Temperature of the reaction is from about −50° C. to about +150° C., preferably from about 80° C. to about 110° C. This reaction may be carried out in the presence of an inert solvent, for instance benzene, toluene, xylene or dioxane.

Thiono hydrazines in which $R_1$ is $NR_3R_4$ may be prepared from the thiono hydrazines in which $R_1$ is thioalkyl by reaction with an appropriate amine. This process is carried out in the presence of a solvent, preferably an alcoholic solvent, but optionally another solvent such as dimethylformamide, toluene, or 1,2-dichloroethane. The temperature of this reaction is from about −50° C. to about +150° C., preferably from about 80° C. to about 110° C.

The following represent examples of processes of type B.

EXAMPLE 2

2-(Acetyl)imino-3-(3-trifluoromethyl)phenyl-5-methylthio-2,3-dihydro-1,3,4-thiadiazole (Compound 44 herein)

a) Production of Thiono hydrazine

In a one liter flask were placed 200 ml of toluene, 14 ml of triethylamine (0.1 mole) and 17.6 g of (3-trifluoromethyl)phenyl hydrazine (0.1 mole). This solution was cooled in an ice bath and 10 ml of carbon disulfide (0.167 mole) was added rapidly but dropwise. This solution was stirred one hour, then 10 ml of dimethyl sulfate (0.106 mole) was added rapidly but dropwise (there was a slight exotherm). The mixture was stirred overnight at ambient temperature. To this mixture was added 250 ml water and 200 ml of diethyl ether. The reaction was separated, dried over magnesium sulfate and the ether removed at reduced pressure to yield solids which were washed in pentane to yield 17.2 g of solids (m.p. 148°–149° C.).

b) Cyclization to Iminothiadiazole intermediate

In a 250 ml flask were placed 8.0 g (0.03 mole) of the product of step (a) and 50 ml of toluene. This was cooled in an ice bath and 4.1 g of cyanogen bromide (0.04 mole) in 50 ml of toluene added. The mixture was stirred several hours at ambient temperature. The solids were collected by filtration to yield 7.1 g.

c) Acylation

In a 100 ml flask were placed 3.7 g of the solid just obtained (0.01 mole), 20 ml of methylene chloride and 0.8 ml of acetyl chloride (0.011 mole). This solution was then cooled in an ice bath and 2.2 ml of pyridine (0.022 mole) was added dropwise. The solution was stirred one hour and worked up in the usual manner to yield 3.2 g of solids, m.p. 95°–97° C.

EXAMPLE 3

2-(Carboethoxy)imino-3-(3-trifluoromethyl)phenyl-5-dimethylamino-2,3-dihydro-1,3,4-thiadiazole (Compound 82 herein)

a) Preparation of Thiono hydrazine

In a one liter flask were placed 50.5 g (0.19 mole) of 1-methyldithiocarbonyl-2-(3-trifluoromethyl)phenyl hydrazine (prepared as in Example 2a), 350 ml of ethanol and 83 ml (0.6 mole) of 40% aqueous dimethylamine. The solution was refluxed for 5 hours and the solvent stripped. The solids were washed with ether to collect 33.9 g of solids, m.p. 162°–168° C.

b) Cyclization

In a 500 ml flask were placed 11.9 g (0.045 mole) of the product from above and 120 ml of toluene. This solution was then cooled in an ice bath and 5.3 g (0.05 mole) of cyanogen bromide in 40 ml of toluene was added dropwise. The slurry was stirred overnight and filtered to collect 15.7 g of the solid hydrobromide salt.

c) Acylation

In a 100 ml flask were placed 3.4 g (0.009 mole) of the solids obtained in step (b), 20 ml of ethylene chloride and 1.0 ml of ethyl chloroformate (0.01 mole). This mixture was cooled in an ice bath and 1.6 ml (0.02 mole) of pyridine dissolved in 5 ml dichloromethane added dropwise with stirring. The mixture was stirred 1 hour and washed with water, separated, dried and stripped to yield 3.2 g of solids (m.p. 92°–93° C.), identified as the expected product.

EXAMPLE 4

2-(Carboisopropoxy)imino-3-(3-trifluoromethyl)phenyl-5-ethoxy-2,3-dihydro-1,3,4-thiadiazole (Compound 83 herein)

a) Preparation of dithiocarbonate

In a 500 ml flask were placed 100 ml of ethanol and 24 g (0.3 mole) of 50% sodium hydroxide. To this stirred solution was added 21 ml (0.35 mole) of carbon disulfide dropwise. This solution was stirred 0.5 hour and 33 ml (0.35 moles) of dimethyl sulfate was added dropwise. The mixture was stirred overnight at ambient temperature. The ethanol was stripped and the residue taken up in ether, washed with water, dried and stripped to yield 34 g.

b) Preparation of Thiono hydrazine

In a 200 ml flask were placed 8 g (0.06 mole) of the product of step (a) and 8.8 g (0.05 mole) of (3-trifluoromethyl)phenyl hydrazine. The solution was heated on a steam bath for 5 hours then stripped to remove low boilers, yielding 15.2 g of a thick oil.

c) Cyclization

The product of step (a) was dissolved in 150 ml of toluene and 6.1 g (0.06 mole) of cyanogen bromide added in one portion. This mixture was stirred overnight and filtered to collect 7 of solid hydrobromide.

d) Acylation

In a 100 ml flask were placed 3.5 g (0.01 mole) of the product of step (c), 20 ml of methylene chloride and 1.2 ml (0.011 mole) of isopropyl chloroformate. This mixture was stirred and cooled in an ice bath, and 1.7 ml (0.21 mole) of pyridine in 5 ml methylene chloride was added dropwise. This mixture was stirred one hour and worked up in the usual manner to yield 3.3 g of solid, m.p. 105°–111° C., identified as the expected product.

EXAMPLE 5

2-(Carbo-n-propoxy)imino-3-(3-trifluoromethyl)phenyl-5-ethyl-2,3-dihydro-1,3,4-thiadiazole (Compound 117 herein)

a) Preparation of Thiono hydrazine

In a 2 liter flask were placed 50 g (0.28 mole) of (3-trifluoromethyl)phenyl hydrazine, 250 ml methylene chloride, 250 ml of 20% sodium hydroxide and 250 g of ice. The stirred mixture was cooled in an ice bath and 25 ml (0.28 mole) of propionyl chloride added dropwise. After addition, this mixture was stirred one hour, phase separated, dried over magnesium sulfate and the organics stripped to collect 54 g solids. In a one liter flask was placed 25 g (0.11 mole) of the solids just obtained and 350 ml benzene. With stirring, 50 g of $P_4S_{10}$ was added and the slurry heated to reflux for 0.25 hour. Twenty ml of water was then carefully added, followed by another 350 ml of water. The mixture was refluxed until the solids all dissolved, then cooled and phase separated. The organic layer was dried, and the solvent stripped to yield 29 g of the expected intermediate.

b) Cyclization

This material (0.12 mole) was then dissolved in 125 ml of toluene and cooled in an ice bath. With stirring was added 8 g (0.13 mole) of cyanogen chloride in 30 ml of toluene. The mixture was stirred overnight at ambient temperature, then filtered to yield 11 g of solid hydrochloride.

c) Acylation

In a 100 ml flask were placed 3.7 g (0.012 mole) of the product of step (b), 15 ml methylene chloride and 1.5 ml (0.013 mole) n-propyl chloroformate. The stirred mixture was cooled in an ice bath and 2.1 ml (0.026 mole) of pyridine added dropwise. The mixture was stirred one hour, washed with water and phase separated. The organics were dried and stripped to yield 3.0 g solids (m.p. 53°–56° C.), identified as the expected product.

Other Processes

Herbicidal compounds in which $R_1$ is alkylsulfinyl or alkylsulfonyl are prepared by oxidation or corresponding compounds in which $R_1$ is alkylthio, under conventional conditions for such oxidations.

Herbicidal compounds in which $R_1$ is cyano, carbamyl or monoalkylcarbamyl are prepared through the corresponding dihydrothiadiazoles in which $R_1$ is $C_1$–$C_2$ carboalkoxy. These are prepared using process B. The thiono hydrazines in which $R_1$ is $C_1$–$C_2$ carboalkoxy are prepared by reacting the appropriate phenyl hydrazine with methyl or ethyl oxalyl chloride or dimethyl or diethyl oxalate, then reacting the product with phosphorus pentasulfide, as in production of thiono hydrazines in which $R_1$ is an alkyl group.

The herbicidal compounds in which $R_1$ is carbamyl or $C_1$–$C_4$ monoalkylcarbamyl are prepared by reacting those compounds in which $R_1$ is carboalkoxy with ammonia or a mono-alkyl amine, respectively. Compounds in which $R_1$ is cyano are prepared by dehydration of the corresponding carbamyl compounds under conventional conditions.

The compounds in which $R_1$ is $C_1$–$C_2$ carboalkoxy are useful as intermediates for preparation of the corresponding cyano, carbamyl or mono-alkylcarbamyl ones.

The following Table I depicts representative compounds of this invention.

TABLE I

Thiadiazoles

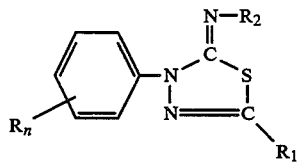

| Cmpd. No. | R | $R_1$ | $R_2$ | m.p. °C. or $n_D^{30}$ |
|---|---|---|---|---|
| 1 | 3-$CF_3$ | $NHCH_3$ | 3-$CF_3$—$C_6H_4$ | oil |
| 2 | 3-$CF_3$ | $NHCH_3$ | 4-F—$C_6H_4$ | semi-solid |
| 3 | 3-$CF_3$ | $NHCH_3$ | 4-Cl—$C_6H_4$ | semi-solid |
| 4 | 3-$CF_3$ | $NHCH_3$ | 4-Br—$C_6H_4$ | semi-solid |
| 5 | 3-$CF_3$ | $NHCH_3$ | 3,4-Cl—$C_6H_3$ | semi-solid |
| 6 | 3-$CF_3$ | $N(CH_3)_2$ | 4-F—$C_6H_4$ | 105–110 |
| 7 | 3-$CF_3$ | $SCH_3$ | 4-F—$C_6H_4$ | 105–110 |
| 8 | 3-$CF_3$ | $N(CH_3)_2$ | 3-$CF_3$—$C_6H_4$ | 85–94 |
| 9 | 3-$CF_3$ | $N(CH_3)_2$ | 4-Br—$C_6H_4$ | 140–146 |
| 10 | 3-$CF_3$ | $N(CH_3)_2$ | 3,4-Cl—$C_6H_3$ | 103–110 |
| 11 | 3-$CF_3$ | $N(CH_3)_2$ | 4-Cl—$C_6H_4$ | 129–137 |
| 12 | 3-$CF_3$ | $N(CH_3)_2$ | 4-CN—$C_6H_4$ | 166–168 |
| 13 | 3-$CF_3$ | $SCH_3$ | 3-$CF_3$—$C_6H_4$ | 95–98 |
| 14 | 3-$CF_3$ | $SCH_3$ | 4-Br—$C_6H_4$ | 125–129 |
| 15 | 3-$CF_3$ | $SCH_3$ | 3,4-Cl—$C_6H_3$ | 66–75 |
| 16 | 3-$CF_3$ | $SCH_3$ | 4-Cl—$C_6H_4$ | 114–124 |
| 17 | 3-$CF_3$ | $SCH_3$ | 4-CN—$C_6H_4$ | 128–135 |
| 18 | 3-$CF_3$ | $SCH_3$ | C(O)NH-i-$C_3H_7$ | 126–127 |
| 19 | 3-$CF_3$ | $SCH_3$ | COO-i-$C_3H_7$ | 87–90 |
| 20 | 3-$CF_3$ | $SCH_3$ | C(O)-i-$C_4H_9$ | 75–78 |
| 21 | 3-$CF_3$ | $N(CH_3)_2$ | COO-i-$C_3H_7$ | 130–133 |
| 22 | 3-$CF_3$ | $SCH_3$ | $COOC_2H_5$ | 59–62 |
| 23 | 3-$CF_3$ | $SCH_3$ | C(O)—S-i-$C_3H_7$ | 57–62 |
| 24 | 3-$CF_3$ | $SCH_3$ | —C(O)$CH_2$—cyclopentyl | 60–64 |
| 25 | 3-$CF_3$ | $SCH_3$ | COO-i-$C_4H_9$ | 1.5770 |
| 26 | 3-$CF_3$ | $SCH_3$ | C(O)$NHCH_3$ | 113–116 |
| 27 | 3-$CF_3$ | $SCH_3$ | C(O)-i-$C_3H_7$ | 85–87 |
| 28 | 3-$CF_3$ | $SCH_3$ | C(O)$SC_2H_5$ | 73–79 |
| 29 | 3-$CF_3$ | $SCH_3$ | C(O)NH-n-$C_3H_7$ | 111–113 |
| 30 | 3-$CF_3$ | $C_2H_5$ | COO-i-$C_3H_7$ | 69–72 |
| 31 | 3-$CF_3$ | $OCH_3$ | COO-i-$C_3H_7$ | 98–100 |
| 32 | 3-$CF_3$ | $OCH_3$ | C(O)NH-i-$C_3H_7$ | 163–165 |
| 33 | 3-$CF_3$ | $OCH_3$ | C(O)-i-$C_4H_9$ | 35–38 |
| 34 | 3-$CF_3$ | $N(CH_3)_2$ | C(O)-i-$C_4H_9$ | 1.5637 |
| 35 | 3-$CF_3$ | $SC_2H_5$ | C(O)—S-i-$C_3H_7$ | oil |
| 36 | 3-$CF_3$ | $SC_2H_5$ | C(O)NH-i-$C_3H_7$ | 135–138 |
| 37 | 3-$CF_3$ | $SC_2H_5$ | COO-i-$C_3H_7$ | 78–81 |
| 38 | 3-$CF_3$ | $SC_2H_5$ | C(O)-i-$C_4H_9$ | semi-solid |
| 39 | 3-$CF_3$ | $SC_2H_5$ | C(O)-n-$C_3H_7$ | 54–58 |
| 40 | 3-$CF_3$ | $N(CH_3)_2$ | C(O)NH-i-$C_3H_7$ | 160–162 |
| 41 | 3-$CF_3$ | $OCH_3$ | C(O)—S-i-$C_3H_7$ | 52–60 |
| 42 | 3-$CF_3$ | $OCH_3$ | $COOC(CH_3)=CH_2$ | 86–90 |

TABLE I-continued

Thiadiazoles

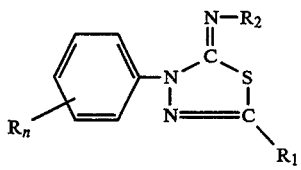

| Cmpd. No. | R | $R_1$ | $R_2$ | m.p. °C. or $n_D^{30}$ |
|---|---|---|---|---|
| 43 | 3-$CF_3$ | $OCH_3$ | $C(O)CH=C(CH_3)_2$ | 107–111 |
| 44 | 3-$CF_3$ | $SCH_3$ | $C(O)CH_3$ | 95–97 |
| 45 | 3-$CF_3$ | $SCH_3$ | $C(O)CH=C(CH_3)_2$ | 99–100 |
| 46 | 3-$CF_3$ | $SCH_3$ | $C(O)CH_2$-C$_6H_4$-F | 94–96 |
| 47 | 3-$CF_3$ | $SCH_3$ | $COOC(CH_3)=CH_2$ | 90–96 |
| 48 | 3-$CF_3$ | $SCH_3$ | $C(O)NHC_2H_5$ | 78–84 |
| 49 | 3-$CF_3$ | $N(CH_3)_2$ | $C(O)-S-i-C_3H_7$ | 98–102 |
| 50 | 3-$CF_3$ | $N(CH_3)_2$ | $C(O)CH=C(CH_3)_2$ | 118–121 |
| 51 | 3-$CF_3$ | $SCH_3$ | $C(O)-i-C_5H_{11}$ | 1.6324 |
| 52 | 3-$CF_3$ | $SCH_3$ | $C(O)CH_2CH(CH_3)C_2H_5$ | 107–111 |
| 53 | 3-$CF_3$ | $SCH_3$ | $C(O)$-C$_6H_4$-F | 48–52 |
| 54 | 3-$CF_3$ | $SCH_3$ | $C(O)$-n-$C_3H_7$ | 45–48 |
| 55 | 3-$CF_3$ | $SCH_3$ | $C(O)CH_2CH(CH_3)CF_3$ | 1.5855 |
| 56 | 3-Cl | $SCH_3$ | $C(O)O$-i-$C_3H_7$ | wax |
| 57 | 3-Cl | $SCH_3$ | $C(O)$-i-$C_4H_9$ | 1.6290 |
| 58 | 3-Cl | $SCH_3$ | $C(O)NH$-i-$C_3H_7$ | wax |
| 59 | 3,4-Cl | $SCH_3$ | $COO$-i-$C_3H_7$ | 98–101 |
| 60 | 3,4-Cl | $SCH_3$ | $COO$-i-$C_4H_9$ | wax |
| 61 | 3,4-Cl | $SCH_3$ | $C(O)NH$-i-$C_3H_7$ | 125–128 |
| 62 | 3-F | $SCH_3$ | $COO$-i-$C_3H_7$ | wax |
| 63 | 3-F | $SCH_3$ | $C(O)$-i-$C_4H_9$ | wax |
| 64 | 3-F | $SCH_3$ | $C(O)NH$-i-$C_3H_7$ | wax |
| 65 | 2-F | $SCH_3$ | $C(O)$-i-$C_4H_9$ | wax |
| 66 | 2-F | $SCH_3$ | $C(O)NH$-i-$C_3H_7$ | 140–144 |
| 67 | 4-F | $SCH_3$ | $COO$-i-$C_3H_7$ | wax |
| 68 | 4-F | $SCH_3$ | $C(O)$-i-$C_4H_9$ | 1.6000 |
| 69 | 4-F | $SCH_3$ | $C(O)NH$-i-$C_3H_7$ | 124–126 |
| 70 | 3-$CF_3$ | $OCH_3$ | $COOCH_3$ | 126–129 |
| 71 | 3-$CF_3$ | $OCH_3$ | $COOC_2H_5$ | 84–87 |
| 72 | 3-$CF_3$ | $OCH_3$ | $COO$-n-$C_3H_7$ | 49–52 |
| 73 | 3-$CF_3$ | $OCH_3$ | $COO$-i-$C_4H_9$ | 43–47 |
| 74 | 3-$CF_3$ | $OCH_3$ | $COO$-n-$C_5H_{11}$ | 1.5454 |
| 75 | 3-$CF_3$ | $OCH_3$ | $COO$-n-$C_4H_9$ | 43–47 |
| 76 | 3-$CF_3$ | $OCH_3$ | $COOCH_2CH=CH_3$ | 60–76 |
| 77 | 3-$CF_3$ | $OCH_3$ | $COO$-sec-$C_5H_{11}$ | 41–46 |
| 78 | 3-$CF_3$ | $OCH_3$ | $COO$-sec-$C_4H_9$ | 85–87 |
| 79 | 3-$CF_3$ | $OCH_3$ | $COOCH_2CH_2Cl$ | 66–69 |
| 80 | 3-$CF_3$ | $OCH_3$ | $COOCH_2CH_2OCH_3$ | 55–59 |
| 81 | 3-$CF_3$ | $N(CH_3)_2$ | $COO$-sec-$C_4H_9$ | 129–131 |
| 82 | 3-$CF_3$ | $N(CH_3)_2$ | $COOC_2H_5$ | 92–93 |
| 83 | 3-$CF_3$ | $OC_2H_5$ | $COO$-i-$C_3H_7$ | 105–111 |
| 84 | 3-$CF_3$ | $OC_2H_5$ | $C(O)$-i-$C_4H_9$ | semi-solid |
| 85 | 3-$SCF_3$ | $OCH_3$ | $COO$-i-$C_3H_7$ | 1.5485 |
| 86 | 3-$SCF_3$ | $OCH_3$ | $C(O)$-i-$C_4H_9$ | 39–46 |
| 87 | 3-$CF_3$ | $N(CH_3)n$-$C_3H_7$ | $COO$-i-$C_3H_7$ | 75–85 |
| 88 | 3-$CF_3$ | $N(CH_3)n$-$C_3H_7$ | $C(O)$-i-$C_4H_9$ | 1.5375 |
| 89 | 3-$SCF_3$ | $SCH_3$ | $COO$-i-$C_3H_7$ | 80–84 |
| 90 | 3-$SCF_3$ | $SCH_3$ | $C(O)$-i-$C_4H_9$ | 45–48 |
| 91 | 3-Cl | $OCH_3$ | $COO$-i-$C_3H_7$ | 68–72 |
| 92 | 3-Cl | $OCH_3$ | $C(O)$-i-$C_4H_9$ | 1.5790 |
| 93 | 3-Cl | $OCH_3$ | $C(O)NH$-i-$C_3H_7$ | 119–121 |
| 94 | 3-Cl | $OCH_3$ | $C(O)-S$-i-$C_3H_7$ | 77–81 |
| 95 | 3-Cl | $OCH_3$ | $COOC_2H_5$ | 121–123 |
| 96 | 3-Cl | $OCH_3$ | $COO$-sec-$C_4H_9$ | 50–59 |
| 97 | 3-$CF_3$ | $OCH_3$ | $COOCH(C_2H_5)_2$ | 66–73 |

TABLE I-continued

Thiadiazoles

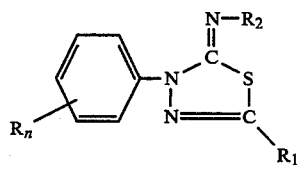

| Cmpd. No. | R | $R_1$ | $R_2$ | m.p. °C. or $n_D^{30}$ |
|---|---|---|---|---|
| 98 | 3-$CF_3$ | $OCH_3$ | COO-cyclopentyl | 94–97 |
| 99 | 3-$CF_3$ | $OCH_3$ | 4-F—$C_6H_5$ | 113–115 |
| 100 | 3-$CF_3$ | $N(CH_3)_2$ | $C(O)CH_2CH(CH_3)CF_3$ | 61–64 |
| 101 | 3-Cl | $OCH_3$ | $C(O)CH_2CH(CH_3)CF_3$ | 69–71 |
| 102 | 3-$CF_3$ | $OCH_3$ | $C(O)CH_3$ | 76–80 |
| 103 | 3-$CF_3$ | $OCH_3$ | $C(O)C_2H_5$ | semi-solid |
| 104 | 3-$CF_3$ | $OCH_3$ | $C(O)$-n-$C_3H_7$ | 1.5402 |
| 105 | 3-$CF_3$ | $OCH_3$ | $C(O)$-i-$C_5H_{11}$ | 1.5243 |
| 106 | 3-$CF_3$ | $OCH_3$ | $C(O)CH_2CH(CH_3)CF_3$ | 52–54 |
| 107 | 3-$CF_3$ | $OCH_3$ | $C(O)CH_2CH_2CH_2Cl$ | 38–39 |
| 108 | 3-$CF_3$ | $OCH_3$ | $COOCH_2CCl_3$ | 73–79 |
| 109 | 3-$CF_3$ | $OCH_3$ | $COOC_6H_5$ | 128–133 |
| 110 | 3-$CF_3$ | $OCH_3$ | COO-n-$C_6H_{13}$ | 1.5181 |
| 111 | 3-$CF_3$ | $OCH_3$ | $C(O)$-sec-$C_5H_{11}$ | 1.5307 |
| 112 | 3-$CF_3$ | $OCH_3$ | $COOCH_2C_6H_5$ | 93–100 |
| 113 | 3-$CF_3$ | $OCH_3$ | $C(O)CF_2CF_2CF_3$ | 65–67 |
| 114 | 3-$CF_3$ | $OCH_3$ | $SO_2$-n-$C_3H_7$ | semi-solid |
| 115 | 3-$CF_3$ | $C_2H_5$ | COO-cyclopentyl | 94–96 |
| 116 | 3-$CF_3$ | $C_2H_5$ | $C(O)$-i-$C_4H_9$ | 1.5210 |
| 117 | 3-$CF_3$ | $C_2H_5$ | COO-n-$C_3H_7$ | 53–56 |
| 118 | 3-$CF_3$ | $C_2H_5$ | COO-i-$C_4H_9$ | 1.5250 |
| 119 | 3-$CF_3$ | $OCH_3$ | COO-(2-methylcyclopentyl) | 1.5340 |
| 120 | 3-$CF_3$ | $OCH_3$ | COO-(3-methylcyclohexyl) | 1.5348 |
| 121 | 3-$CF_3$ | $OCH_3$ | COO-cyclohexyl | 82.88 |
| 122 | 3-$CF_3$ | $N(CH_3)_2$ | COO-(2-methylcyclopentyl) | 122–124 |
| 123 | 3-$CF_3$ | $SCH_3$ | $C(O)NHC_6H_5$ | 161–163 |
| 124 | 3-$CF_3$ | $NHCH_3$ | COO-i-$C_3H_7$ | 141–156 |
| 125 | 3-$CF_3$ | $CH_3$ | COO-i-$C_3H_7$ | 113–118 |
| 126 | 3-$CF_3$ | $CH_3$ | $C(O)$-i-$C_4H_9$ | waxy solid |
| 127 | 3-$CF_3$ | $OCH_3$ | $COOCH(CH_3)CH(CH_3)_2$ | 85–88 |

TABLE I-continued
Thiadiazoles

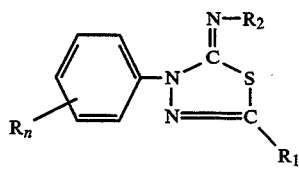

| Cmpd. No. | R | $R_1$ | $R_2$ | m.p. °C. or $n_D^{30}$ |
|---|---|---|---|---|
| 128 | 3-$CF_3$ | $OCH_3$ | (3-methylcyclopentyl)-COO- | 1.5365 |
| 129 | 3-$CF_3$ | $OCH_3$ | (tetrahydrofuran-3-yl)-COO- | 94–95 |
| 130 | 3-$CF_3$ | $OCH_3$ | CN | 83–86 |
| 131 | 3-$CF_3$ | $OCH_3$ | $C(O)CH_2COOC_2H_5$ | 50–54 |
| 132 | 3-$CF_3$ | $OCH_3$ | $SO_2CH_2Cl$ | 102–105 |
| 133 | 3-$CF_3$ | CN | COO-i-$C_3H_7$ | 93–96 |
| 134 | 3-$CF_3$ | $OCH_3$ | $C(S)NHCH_3$ | 150–154 |
| 135 | 3-$CF_3$ | $OCH_3$ | (tetrahydropyran-2-yl)-$CH_2$OOC- | 83–87 |
| 136 | 3-$CF_3$ | $OCH_3$ | (tetrahydrofuran-2-yl)-$CH_2$OOC- | 63–70 |
| 137 | 3-$CF_3$ | $OCH_3$ | (furan-2-yl)-$CH_2$OOC- | 84–86 |
| 138 | 3-$CF_3$ | $OCH_3$ | $C(O)NH$—$CH_3$ | 119–122 |
| 137 | 3-$CF_3$ | $OCH_3$ | $CH$=$CHC(O)CH_3$ | 79–81 |
| 140 | 3-$CF_3$ | $OCH_3$ | $C(O)N(CH_3)_2$ | 99–103 |
| 141 | 3-$CF_3$ | $OCH_3$ | $C(O)$-cyclopropyl | 79–81 |
| 142 | 3-$CF_3$ | $OCH_3$ | $C(O)$-cyclohexyl | 89–97 |
| 143 | 3-$CF_3$ | $N(CH_3)_2$ | COO-i-$C_3H_7$ | 57–64 |
| 144 | 3-$CF_3$ | $C(O)NH_2$ | COO-i-$C_3H_7$ | 186–195 |
| 145 | 3-$CF_3$ | $OCH_3$ | (2,2-dimethyl-1,3-dioxolan-4-yl)-$CH_2$OOC- | 1.5332 |
| 146 | 3-$CF_3$ | $OCH_3$ | COO-t-$C_4H_9$ | 113–118 |
| 147 | 3-$CF_3$ | $OCH_3$ | $C(O)N(CH_3)(C_2H_5)$ | 55–59 |

TABLE I-continued
Thiadiazoles
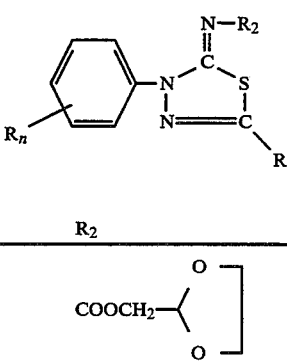
| Cmpd. No. | R | $R_1$ | $R_2$ | m.p. °C. or $n_D^{30}$ |
|---|---|---|---|---|
| 148 | 3-$CF_3$ | $OCH_3$ | 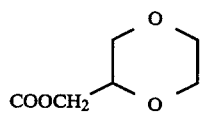 | 95–91 |
| 149 | 3-$CF_3$ | $OCH_3$ | 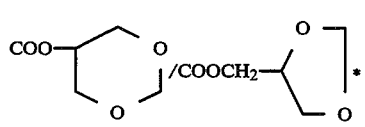 | 112–113 |
| 150 | 3-$CF_3$ | $OCH_3$ | 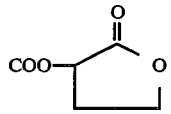 | 79–90.5 |
| 151 | 3-$CF_3$ | $OCH_3$ | $COOCH(CH_3)COOCH_3$ | 97–99 |
| 152 | 3-$CF_3$ | $OCH_3$ | $C(O)CH_2Cl$ | 65–68 |
| 153 | 3-$CF_3$ | $OCH_3$ | $SO_2CH_3$ | 114–115 |
| 154 | 3-$CF_3$ | $OCH_3$ | 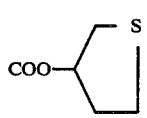 | 140–141 |
| 155 | 3-$CF_3$ | $OCH_3$ | 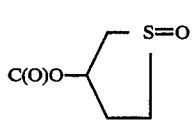 | 105–106 |
| 156 | 3-$CF_3$ | $OCH_3$ | 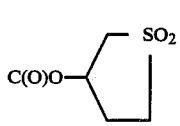 | 61–65 |
| 157 | 3-$CF_3$ | $OCH_3$ | 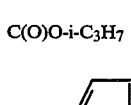 | 149–151 |
| 158 | 3-$CF_3$ | $C(O)NHCH_3$ | $C(O)O$-i-$C_3H_7$ | 196.5–200.5 |
| 159 | 3-$CF_3$ | $OCH_3$ | 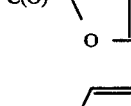 | 160.3–163.6 |
| 160 | 3-$CF_3$ | $OCH_3$ | 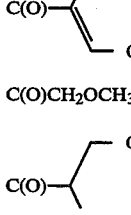 | 136.2–137.9 |
| 161 | 3-$CF_3$ | $OCH_3$ | $C(O)CH_2OCH_3$ | 61.8–64.1 |
| 162 | 3-$CF_3$ | $OCH_3$ | 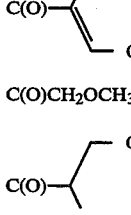 | 99.6–100.6 |

TABLE I-continued

Thiadiazoles

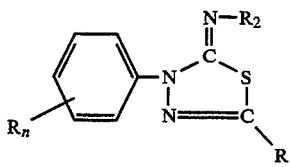

| Cmpd. No. | R | $R_1$ | $R_2$ | m.p. °C. or $n_D^{30}$ |
|---|---|---|---|---|
| 163 | 3-$CF_3$ | $SO_2CH_3$ | $C(O)CH_2CH(CH_3)_2$ | 121.6–123.7 |
| 164 | H | $SCH_3$ | $C(O)O$-$i$-$C_3H_7$ | 101.3–103.9 |
| 165 | H | $SCH_3$ | $C(O)$-$i$-$C_4H_9$ | 1.6055 |
| 166 | H | $SCH_3$ | $C(O)NH$-$i$-$C_3H_7$ | 120.5–123.8 |
| 167 | 3-$CH_3$ | $SCH_3$ | $C(O)O$-$i$-$C_3H_7$ | 1.6053 |
| 168 | 3-$CH_3$ | $SCH_3$ | $C(O)$-$i$-$C_4H_9$ | oil |
| 169 | 3-$CH_3$ | $SCH_3$ | $C(O)NH$-$i$-$C_3H_7$ | 74.4–79.7 |
| 170 | 3-$OCH_3$ | $SCH_3$ | $C(O)O$-$i$-$C_3H_7$ | oil |
| 171 | 3-$OCH_3$ | $SCH_3$ | $C(O)NH$-$i$-$C_3H_7$ | 109.9–111.8 |
| 172 | 3-$CF_3$ | $SCH_3$ | 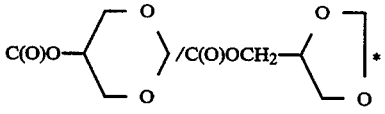 | 100.6–107.8 |
| 173 | 3-$CF_3$ | $SCH_3$ | 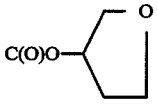 | 72.6–75.8 |
| 174 | 3-$CF_3$,4-F | $SCH_3$ | $C(O)O$-$i$-$C_3H_7$ | 105.5–107.7 |
| 175 | 3-$CF_3$,4-F | $SCH_3$ | $C(O)$-$i$-$C_4H_9$ | 42.9–51.0 |
| 176 | 3-$CF_3$,4-F | $SCH_3$ | $C(O)NH$-$i$-$C_3H_7$ | 135.8–136.5 |
| 177 | 3-$SCH_3$ | $SCH_3$ | $C(O)O$-$i$-$C_3H_7$ | 1.5275 |
| 178 | 3-$SCH_3$ | $SCH_3$ | $C(O)NH$-$i$-$C_3H_7$ | semi-solid |
| 179 | 3-Cl,4-F | $SCH_3$ | $C(O)O$-$i$-$C_3H_7$ | 110.8–112.8 |
| 180 | 3-Cl,4-F | $SCH_3$ | $C(O)$-$i$-$C_4H_9$ | 52.6–55.9 |
| 181 | 3-Cl,4-F | $SCH_3$ | $C(O)NH$-$i$-$C_3H_7$ | 81.3–92.8 |
| 182 | 3-$CF_3$ | $S(O)CH_3$ | $C(O)$-$i$-$C_4H_9$ | 86.2–92.1 |
| 183 | 3-$SCH_3$ | $OCH_3$ | $C(O)O$-$i$-$C_3H_7$ | 1.5436 |
| 184 | 3-Cl,4-F | $OCH_3$ | $C(O)$-$i$-$C_4H_9$ | 49.0–59.2 |
| 185 | 3-Cl,4-F | $OCH_3$ | $C(O)$-$i$-$C_3H_7$ | 127.3–129.0 |
| 186 | 3-Cl,4-F | $OCH_3$ | 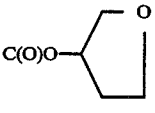 | 125.9–127.4 |
| 187 | 3-$SO_2CH_3$ | $OCH_3$ | $C(O)O$-$i$-$C_3H_7$ | 144.5–146.2 |
| 188 | 3-$CF_3$,4-F | $OCH_3$ | $C(O)O$-$i$-$C_3H_7$ | 98.6–101.0 |
| 189 | 3-$CF_3$,4-F | $OCH_3$ | $C(O)$-$i$-$C_4H_9$ | 54.9–58.0 |
| 190 | 3-$CF_3$,4-F | $OCH_3$ | 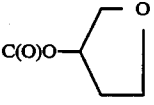 | 106.1–109.8 |
| 191 | 3-$CF_3$ | —$SCH_3$ | 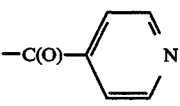 | 132.0–136.0 |
| 192 | 3-$OCF_3$ | —$OCH_3$ | —$C(O)$—$O$-$i$-$C_3H_7$ | light oil |
| 193 | 3-$OCF_2H$ | —$OCH_3$ | —$C(O)O$-$i$-$C_3H_7$ | 1.5485 |
| 194 | 3-$OCF_2CF_2H$ | —$SCH_3$ | 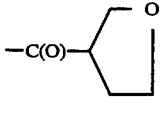 | 79.7–82.8 |
| 195 | 3-$OCF_2CF_2H$ | —$SCH_3$ | —$C(O)O$-$i$-$C_3H_7$ | 82.5–85.7 |

TABLE I-continued

Thiadiazoles

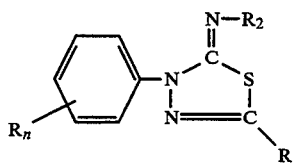

| Cmpd. No. | R | $R_1$ | $R_2$ | m.p. °C. or $n_D^{30}$ |
|---|---|---|---|---|
| 196 | 3-OCF$_2$CF$_2$H | —SCH$_3$ | —C(O)-i-C$_4$H$_9$ | 57.4–62.9 |
| 197 | 3-OCF$_2$CF$_2$H | —OCH$_3$ | —C(O)-i-C$_3$H$_7$ | 88.6–89.4 |
| 198 | 3-OCF$_2$CF$_2$H | —OCH$_3$ | —C(O)-i-C$_4$H$_9$ | 81.4–83.8 |
| 199 | 3-OCF$_2$CF$_2$H | —OCH$_3$ | —C(O)-i-C$_4$H$_9$ | 50.0–51.8 |
| 200 | 3-OCF$_2$CF$_2$H | —OCH$_3$ | —C(O)-cyclopropyl | 1.5410 |
| 201 | 3-OCF$_2$CF$_2$H | —OCH$_3$ | —C(O)-(1-methylcyclopropyl) | 80.9–90.6 |
| 202 | 3-OCF$_2$CF$_2$H | —OCH$_3$ | —C(O)-(2-methylcyclopropyl) | 1.5330 |
| 203 | 3-CF$_3$-4-F | —OCH$_3$ | —C(O)-cyclopropyl | 99.7–102.4 |
| 204 | 3-CF$_3$-4-F | —OCH$_3$ | —C(O)-(1-methylcyclopropyl) | 108.9–111.4 |
| 205 | 3-CF$_3$-4-F | —OCH$_3$ | —C(O)-(2-methylcyclopropyl) | 89.6–92.2 |
| 206 | 3-CF$_3$ | —OCH$_3$ | —C(O)-(1-methylcyclopropyl) | 79.7–81.8 |
| 207 | 3-CF$_3$ | —OCH$_3$ | —C(O)-(2-methylcyclopropyl) | 1.5524 |
| 208 | 3-CF$_3$ | —OC$_2$H$_5$ | —C(O)OC$_2$H$_5$ | 88.4–92.5 |
| 209 | 3-CF$_3$ | —OC$_2$H$_5$ | —C(O)C$_3$H$_7$ | semi-solid |
| 210 | 3-CF$_3$ | —OC$_2$H$_5$ | —C(O)—CH$_2$—(4-F-phenyl) | 78.8–80.2 |
| 211 | 3-CF$_3$ | —OC$_2$H$_5$ | —COO—(tetrahydrofuran-3-yl) | 104.9–107.0 |
| 212 | 3-CF$_3$ | H | —C(O)-i-C$_3$H$_7$ | thick oil |
| Iminothiadiazole Intermediates | | | | |
| 213 | 3-CF$_3$ | OCH$_3$ | — | 72–73.5 |
| 214 | hydrobromide of compound No. 191 | | | 144–145 |
| 215 | 3-CF$_3$ | SCH$_3$ | hydrobromide | 222.3–224.2 |

*Produced as a mixture due to mixture of isomers in starting materials.

Herbicidal Evaluation

Compounds of the foregoing Table I were tested for herbicidal activity as follows.

Pre-Emergence Herbicide Screening Test

Flats were filled with sandy loam soil containing a fungicide and fertilizer. The soil was leveled and rows of three grassy weeds, three broadleaf weeds and yellow nutsedge (*Cyperus esculentus*), were planted thickly enough that several seedlings emerged per inch of row. The grassy weeds were: green foxtail (*Setaria viridis*), watergrass (*Echinochola crusgalli*) and wild oat (*Avena fatua*). Broadleaf weeds utilized were annual morning-glory (*Ipomoea purpurea*), velvetleaf (*Abutilon theophrasti*) and wild mustard (*Brassica kaber*).

Solutions of the test compounds were made by weighing out 333 mg of the compound in question into a bottle, and dissolving it in 25 ml of acetone containing 1% polyoxyethylene sorbitan monolaurate emulsifier to form a stock solution. Additional solvents, not exceeding 5 ml, were used if needed to dissolve the compound. An aliquot was taken from the stock solution and diluted with a 19:1 water:acetone mixture containing 1% of the emulsifier to form a sprayable solution.

The flats were placed in a greenhouse at 70°–85° F. (21.1°–29.5° C.) and watered by sprinkling. One day after planting the flats were sprayed with the solutions of the test compounds at a rate of 80 gallons of solution per acre with the compound being applied at a rate of 4 pounds per acre (4.48 kg/ha).

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill.

Post-Emergence Herbicidal Evaluation

The soil was prepared and seeded with the same varieties as described for the pre-emergence test. The flats were placed in the greenhouse at 70°–85° F. (21.1°–29.5° C.) and watered by sprinkling. Twelve to fourteen days after planting, the flats were sprayed on a table at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests in terms of average control of the three grasses and three broadleaf weeds, respectively, in both pre- and post-emergence evaluations. Control of nutsedge is not included in this table for convenience, as most of the compounds showed no or practically no control of nutsedge in these tests. Some compounds, however, notably Compounds 70, 71, 72, 76, 79, 80, 129, 130, 132, 138, 141, 150, 155, 156, 161, 162, 172, 173, 185, 186, 188, 189 and 190 did demonstrate activity against nutsedge.

It should be noted that even those compounds which (from the following table) indicate a relatively low average control of weeds, nevertheless showed good activity against at least one weed in these tests, which in many cases was wild mustard.

TABLE II

| Compound Number | Pre-emergence Control (average) | | Post-emergence Control (average) | |
|---|---|---|---|---|
| | grasses | broadleaf | grasses | broadleaf |
| 1 | 23 | 43 | 10 | 53 |
| 2 | 30 | 73 | 20 | 83 |
| 3 | 28 | 0 | 27 | 47 |
| 4 | 28 | 82 | 7 | 65 |
| 5 | 23 | 67 | 10 | 72 |
| 6 | 0 | 42 | — | — |
| 7 | 73 | 73 | 50 | 78 |
| 8 | 7 | 63 | 30 | 63 |
| 9 | 0 | 37 | 3 | 55 |
| 10 | 2 | 48 | 13 | 73 |
| 11 | 2 | 42 | 13 | 57 |
| 12 | 42 | 85 | 27 | 63 |
| 13 | 20 | 32 | 2 | 23 |
| 14 | 17 | 30 | 2 | 22 |
| 15 | 27 | 35 | 2 | 25 |
| 16 | 33 | 47 | 5 | 25 |
| 17 | 47 | 73 | 13 | 25 |
| 18 | 93 | 83 | 38 | 50 |
| 19 | 95 | 97 | 68 | 60 |
| 20 | 95 | 95 | 80 | 70 |
| 21 | 93 | 93 | 50 | 57 |
| 22 | 93 | 47 | 60 | 67 |
| 23 | 92 | 77 | 65 | 80 |
| 24 | 90 | 63 | 60 | 67 |
| 25 | 93 | 63 | 67 | 73 |
| 26 | 90 | 87 | 63 | 73 |
| 27 | 93 | 90 | 67 | 73 |
| 28 | 92 | 75 | 63 | 63 |
| 29 | 67 | 53 | 37 | 37 |
| 30 | 93 | 95 | 73 | 73 |
| 31 | 97 | 100 | 83 | 78 |
| 32 | 93 | 90 | 63 | 73 |
| 33 | 97 | 100 | 82 | 73 |
| 34 | 95 | 95 | 85 | 85 |
| 35 | 30 | 10 | 10 | 40 |
| 36 | 0 | 0 | 0 | 20 |
| 37 | 40 | 32 | 10 | 33 |
| 38 | 77 | 53 | 53 | 60 |
| 39 | 85 | 53 | 23 | 40 |
| 40 | 33 | 63 | 47 | 50 |
| 41 | 93 | 100 | 87 | 83 |
| 42 | 83 | 73 | 67 | 80 |
| 43 | 93 | 100 | 83 | 80 |
| 44 | 95 | 80 | 80 | 83 |
| 45 | 67 | 63 | 57 | 80 |
| 46 | 37 | 57 | 13 | 47 |
| 47 | 23 | 37 | 13 | 50 |
| 48 | 77 | 93 | 50 | 73 |
| 49 | 28 | 53 | 13 | 47 |
| 50 | 43 | 60 | 10 | 80 |
| 51 | 97 | 88 | 73 | 87 |
| 52 | 97 | 93 | 78 | 77 |
| 53 | 63 | 80 | 20 | 65 |
| 54 | 100 | 93 | 83 | 83 |
| 55 | 100 | 100 | 85 | 92 |
| 56 | 97 | 47 | 27 | 60 |
| 57 | 97 | 85 | 78 | 93 |
| 58 | 90 | 85 | 23 | 90 |
| 59 | 45 | 22 | 10 | 40 |
| 60 | 60 | 42 | 20 | 60 |
| 61 | 35 | 10 | 13 | 50 |
| 62 | 72 | 37 | 13 | 50 |
| 63 | 93 | 67 | 65 | 87 |
| 64 | 87 | 75 | 43 | 77 |
| 65 | 73 | 37 | 13 | 30 |
| 66 | 43 | 33 | 2 | 13 |
| 67 | 83 | 57 | 27 | 67 |
| 68 | 88 | 57 | 43 | 60 |
| 69 | 80 | 28 | 7 | 27 |
| 70 | 100 | 100 | 88 | 80 |

TABLE II-continued

| Compound Number | Pre-emergence Control (average) | | Post-emergence Control (average) | |
|---|---|---|---|---|
| | grasses | broadleaf | grasses | broadleaf |
| 71 | 98 | 100 | 83 | 80 |
| 72 | 98 | 100 | 85 | 80 |
| 73 | 100 | 100 | 87 | 57 |
| 74 | 100 | 100 | 85 | 80 |
| 75 | 100 | 100 | 87 | 80 |
| 76 | 100 | 100 | 87 | 83 |
| 77 | 98 | 100 | 87 | 80 |
| 78 | 98 | 100 | 77 | 83 |
| 79 | 98 | 100 | 85 | 83 |
| 80 | 98 | 97 | 80 | 80 |
| 81 | 70 | 93 | 60 | 77 |
| 82 | 83 | 88 | 72 | 70 |
| 83 | 88 | 82 | 73 | 87 |
| 84 | 100 | 100 | 83 | 83 |
| 85 | 98 | 100 | 87 | 83 |
| 86 | 98 | 100 | 80 | 83 |
| 87 | 72 | 90 | 57 | 80 |
| 88 | 75 | 92 | 47 | 73 |
| 89 | 88 | 83 | 53 | 73 |
| 90 | 95 | 95 | 60 | 73 |
| 91 | 95 | 92 | 67 | 73 |
| 92 | 97 | 100 | 87 | 73 |
| 93 | 93 | 92 | 60 | 60 |
| 94 | 75 | 63 | 47 | 53 |
| 95 | 97 | 97 | 72 | 73 |
| 96 | 95 | 97 | 80 | 73 |
| 98 | 80 | 63 | 60 | 47 |
| 98 | 97 | 97 | 70 | 73 |
| 99 | 85 | 90 | 33 | 73 |
| 100 | 97 | 100 | 73 | 80 |
| 101 | 97 | 98 | 80 | 83 |
| 102 | 98 | 100 | 83 | 80 |
| 103 | 98 | 100 | 80 | 80 |
| 104 | 100 | 98 | 80 | 80 |
| 105 | 98 | 100 | 82 | 80 |
| 106 | 98 | 100 | 82 | 80 |
| 107 | 100 | 100 | 82 | 80 |
| 108 | 98 | 100 | 80 | 80 |
| 109 | 82 | 98 | 33 | 80 |
| 110 | 97 | 97 | 80 | 75 |
| 111 | 98 | 100 | 33 | 87 |
| 112 | 83 | 82 | 27 | 80 |
| 113 | 95 | 87 | 57 | 80 |
| 114 | 95 | 100 | 40 | 80 |
| 115 | 100 | 83 | 67 | 67 |
| 116 | 100 | 100 | 88 | 87 |
| 117 | 100 | 100 | 87 | 87 |
| 118 | 100 | 100 | 87 | 80 |
| 119 | 100 | 100 | 92 | 90 |
| 120 | 100 | 63 | 43 | 67 |
| 121 | 97 | 78 | 85 | 60 |
| 122 | 20 | 75 | 0 | 90 |
| 123 | 5 | 8 | 2 | 53 |
| 124 | 80 | 100 | 70 | 97 |
| 125 | 98 | 100 | 93 | 70 |
| 126 | 98 | 100 | 97 | 100 |
| 127 | 93 | 100 | 53 | 50 |
| 128 | 97 | 100 | 87 | 88 |
| 129 | 100 | 100 | 87 | 87 |
| 130 | 95 | 100 | 95 | 95 |
| 131 | 85 | 40 | 73 | 67 |
| 132 | 100 | 100 | 98 | 93 |
| 133 | 50 | 67 | 27 | 77 |
| 134 | 50 | 30 | 10 | 40 |
| 138 | 100 | 100 | 87 | 57 |
| 139 | 97 | 92 | 60 | 73 |
| 140 | 70 | 100 | 80 | 90 |
| 141 | 100 | 100 | 87 | 90 |
| 142 | 100 | 100 | 87 | 87 |
| 143 | 95 | 97 | 73 | 73 |
| 144 | 87 | 92 | 83 | 80 |
| 145 | 77 | 63 | 63 | 68 |
| 146 | 95 | 100 | 68 | 100 |
| 150 | 100 | 100 | 100 | 100 |
| 151 | 50 | 73 | 47 | 60 |
| 152 | 97 | 70 | 53 | 92 |
| 153 | 70 | 100 | 73 | 63 |
| 154 | 67 | 43 | 20 | 0 |
| 155 | 47 | 70 | 60 | 70 |
| 156 | 97 | 100 | 80 | 87 |
| 157 | 73 | 100 | 87 | 90 |
| 158 | 40 | 40 | 7 | 58 |
| 159 | 77 | 40 | 3 | 33 |
| 160 | 100 | 80 | 23 | 87 |
| 161 | 100 | 100 | 97 | 100 |
| 162 | 100 | 100 | 100 | 100 |
| 163 | 98 | 100 | 67 | 60 |
| 164 | 97 | 40 | 37 | 33 |
| 165 | 100 | 58 | 60 | 50 |
| 166 | 73 | 63 | 37 | 40 |
| 167 | 97 | 47 | 77 | 57 |
| 168 | 100 | 67 | 57 | 73 |
| 169 | 93 | 80 | 60 | 82 |
| 170 | 100 | 63 | 30 | 10 |
| 171 | 93 | 80 | 33 | 23 |
| 172 | 100 | 83 | 80 | 93 |
| 173 | 100 | 93 | 80 | 97 |
| 174 | 100 | 100 | 100 | 100 |
| 175 | 100 | 100 | 100 | 100 |
| 176 | 97 | 95 | 100 | 82 |
| 177 | 83 | 73 | 75 | 60 |
| 178 | 70 | 45 | 73 | 73 |
| 179 | 73 | 50 | 67 | 53 |
| 180 | 87 | 93 | 90 | 53 |
| 181 | 83 | 93 | 80 | 60 |
| 182 | 80 | 70 | 83 | 87 |
| 183 | 100 | 93 | 88 | 83 |
| 184 | 100 | 100 | 93 | 97 |
| 185 | 100 | 100 | 93 | 100 |
| 186 | 100 | 100 | 97 | 97 |
| 187 | 95 | 100 | 93 | 83 |
| 188 | 100 | 100 | 93 | 83 |
| 189 | 100 | 100 | 88 | 80 |
| 190 | 100 | 100 | 87 | 80 |
| 191 | 43 | 73 | 0 | 60 |
| 192* | 100 | 98 | 98 | 85 |
| 193*[a] | 100 | 100 | 93 | 97 |
| 194* | 70 | 87 | 30 | 53 |
| 195* | 50 | 47 | 0 | 37 |
| 196* | 93 | 100 | 67 | 87 |
| 197* | 97 | 100 | 47 | 70 |
| 198* | 93 | 100 | 80 | 80 |
| 199* | 100 | 100 | 95 | 93 |
| 200* | 100 | 100 | 63 | 90 |
| 201* | 100 | 67 | 50 | 80 |
| 202* | 100 | 100 | 100 | 97 |
| 203* | 100 | 100 | 100 | 80 |
| 204* | 100 | 100 | 78 | 80 |
| 205* | 100 | 100 | 100 | 90 |
| 206* | 100 | 100 | 98 | 95 |
| 207* | 100 | 100 | 100 | 63 |
| 208 | 100 | 63 | 53 | 33 |
| 209 | 100 | 93 | 93 | 93 |
| 210 | 60 | 80 | 40 | 37 |
| 211 | 100 | 100 | 90 | 83 |
| 212 | 98 | 85 | 77 | 93 |
| 213 | 95 | 67 | 47 | 67 |
| 214 | 95 | 87 | 73 | 83 |
| 215 | 70 | 33 | 30 | 10 |

[a]Rated at 18 days after treatment.
*Treatment = 2 lb/Acre.

Further Herbicidal Evaluation

Compounds showing good activity in the evaluations described above were submitted for one or more subsequent evaluations involving, for example, different weeds, lower application rates, varying application procedures, and/or selectivity with respect to crops. The weeds employed in these tests included those utilized in the tests just described, as well as a number of others such as one or more species of ryegrass (Lolium), Sorghum, signalgrass (Brachiaria), cocklebur (Xanthium), Sesbania, Cassia, Alopecurus, oats (Avena), bluegrass (Poa), Matricaria, chickweed (Stellaria), bedstraw (Galium), and violet (Viola). Crops which were variously employed in these evaluations included cotton (*Gossypium hirsutum*), soybean (*Glycine max*), corn (*Zea maize*), milo (*Sorghum bicolor*), wheat (*Tritium aestivum*), sugarbeet (*Beta vulgaris*), rice (*Oryza sativa*), carrot (*Daucus carota*), and barley (*Hordeum vulgare*).

In summation, compounds submitted for further evaluation showed varying activity depending on the compound and the evaluation employed. Some compounds showed a better activity in controlling grasses, others in controlling broadleaf weeds. Some compounds demonstrated better activity in pre-emergence application, others in post-emergence application. Some compounds demonstrated good activity in nearly all types of application. Some compounds demonstrated good control in tests at application rates ranging as low as 0.06 pound per acre (0.065 kg/ha).

With respect to injury to crops, nearly all compounds tested produced unacceptable injury to sugarbeets even at relatively low levels of application. Some compounds showed good broad-spectrum activity but relatively low selectivity, causing injury to both weeds and crops in the same tests. Other compounds showed varying selectivity to certain crops, particularly cereals, such as wheat, rice and corn, most notably with respect to rice in various methods of application. A number of compounds also demonstrated selectivity in controlling weeds in the presence of cotton.

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, tablets, powders and the like. Examples of liquid forms a emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolines, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of powder dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Ingredient | Weight % | | |
|---|---|---|---|
| Oil | | | |
| Active Compound | 1 | | |
| Oil solvent-heavy aromatic naphtha | 99 | | |
| Total | 100 | | |
| Emulsifiable Concentrate | | | |
| Active Compound | 50 | | |
| Kerosene | 45 | | |
| Emulsifying agent (mixture of long chain ethoxylated polyethers with long chain sulfonate) | 5 | | |
| Total | 100 | | |
| Active Compound | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A process for producing a compound of the formula

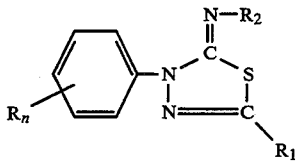

in which

R is halo, trihalomethyl, pentahaloethyl, mono- or difluoromethyl, mono-, di-, tri- or tetrafluoroethyl, fluoroalkylthio, fluoroalkoxy, methylthio, methylsulfonyl, halomethylsulfonyl, $C_1$-$C_2$ alkyl, or methoxy;

n is 1 or 2, provided that:
 (a) is n is 1 and R is other than fluoro, the substituent R is located at the 3-position on the phenyl ring; and
 (b) if n is 2, the substituents R are located at the 3- and 4-positions on the phenyl ring;

$R_1$ is hydrogen, $C_1$-$C_3$ alkyl, $C_1$-$C_3$ alkoxy, $C_1$-$C_2$ alkyl thio, $C_3$-$C_4$ alkenylthio, cyano, carbamyl, $C_1$-$C_4$ mono-alkylcarbamyl, $C_1$-$C_2$ carboalkoxy, or $NR_3R_4$ in which $R_3$ and $R_4$ are independently hydrogen, $C_1$-$C_4$ alkyl or $C_2$-$C_4$ alkenyl; and $R_2$ is hydrogen, comprising reacting a compound having the formula

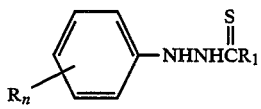

with cyanogen chloride or cyanogen bromide.

2. A process for producing a hydrohalide salt according to claim 1 comprising reacting a compound having the formula

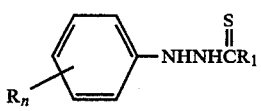

with cyanogen chloride or cyanogen bromide in the presence of a base.

3. A process for producing a compound of the formula

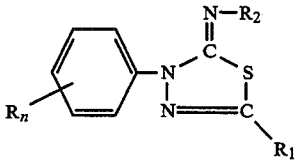

in which

R is halo, trihalomethyl, pentahaloethyl, mono- or difluoromethyl, mono-, di-, tri- or tetrafluoroethyl, fluoro alkylthio, fluoroalkoxy, methylthio, methylsulfonyl, halomethyl sulfonyl, $C_1$-$C_2$ alkyl, or methoxy;

n is 1 or 2, provided that:
 (a) is n is 1 and R is other than fluoro, the substituent R is located at the 3-position on the phenyl ring; and
 (b) if n is 2, the substituents R are located at the 3- and 4-positions on the phenyl ring;

$R_1$ is hydrogen, $C_1$-$C_3$ alkyl, $C_1$-$C_3$ alkoxy, $C_1$-$C_2$ alkylthio, $C_3$-$C_4$ alkenylthio, cyano, carbamyl, $C_1$-$C_4$ mono-alkylcarbamyl, $C_1$-$C_2$ carboalkoxy, or $NR_3R_4$ in which $R_3$ and $R_4$ are independently hydrogen, $C_1$-$C_4$ alkyl or $C_2$-$C_4$ alkenyl; and $R_2$ is $C_1$-$C_4$ mono- or dialkylcarbamyl; phenylcarbamyl; $C_1$-$C_4$ mono-alkylthiocarbamyl; $C_4$-$C_6$ ketoalkenyl; cyano; $C_1$-$C_4$ alkylsulfonyl; $C_1$-$C_4$ haloalkylsulfonyl; or $$\overset{O}{\underset{\|}{C}}-(Y)_m-R_5$$

in which Y is oxygen or sulfur; m is 0 or 1; and $R_5$ is $C_1$-$C_{10}$ alkyl; $C_2$-$C_{10}$ alkenyl; $C_2$-$C_8$ alkynyl if m is 0; $C_3$-$C_8$ alkynyl in which the triple bond is separated from the oxygen or sulfur atom (Y) by at least one methylene group if m is 1; $C_1$-$C_8$ haloalkyl if m is 0; $C_2$-$C_8$ haloalkyl if m is 1; $C_2$-$C_{10}$ alkoxyalkyl if m is 0; pyridyl if m is 0; $C_3$-$C_{10}$ alkoxyalkyl in which the alkylene portion has at least two carbon atoms if m is 1; or $R_5$ is

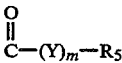

in which p is 0 or 1; $R_6$ is a $C_1$-$C_2$ alkylene group and $R_7$ is phenyl, halo-substituted phenyl, $C_3$-$C_7$ cycloalkyl, optionally substituted by from 1 to 3 methyl groups; $C_1$-$C_4$ carboalkoxy; or a saturated or unsaturated heterocyclic ring containing from 5 to 6 atoms including from 1 to 2 hetero atoms selected from oxygen and sulfur, optionally substituted by from 1 to 3 methyl groups and optionally substituted by from 1 to 2 oxo groups; provided that when $R_1$ is methylthio and $R_2$ is isopropylcarboxy, then R is not 2-fluoro, comprising (a) reacting a compound having the formula

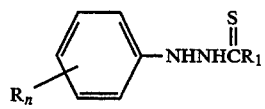

with cyanogen chloride or cyanogen bromide, optionally in the presence of a base; and (b) reacting the product of step (a) with an acylating agent selected from the group consisting of compounds having the formula

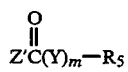

in which $Z'$ is a halogen and isocyanates and isothiocyanates having the formula $R_9$—NCO or $R_9$NCS in which $R_9$ is $C_1$-$C_4$ alkyl or phenyl.

* * * * *